US010105258B2

(12) United States Patent
Dockhom et al.

(10) Patent No.: US 10,105,258 B2
(45) Date of Patent: Oct. 23, 2018

(54) DEVICE FOR RECEIVING AN INTRAOCULAR LENS, AND METHOD FOR FOLDING AN INTRAOCULAR LENS

(71) Applicant: MEDICEL AG, Wolfhalden (CH)

(72) Inventors: Volker Dockhom, Berg (CH); Emil Hohl, Au (CH)

(73) Assignee: MEDICEL AG (CH)

(*) Notice: Subject to any disclaimer, the term of this patent is extended or adjusted under 35 U.S.C. 154(b) by 69 days.

(21) Appl. No.: 14/904,844

(22) PCT Filed: Nov. 17, 2014

(86) PCT No.: PCT/CH2014/000166
§ 371 (c)(1),
(2) Date: Jan. 13, 2016

(87) PCT Pub. No.: WO2015/070358
PCT Pub. Date: May 21, 2015

(65) Prior Publication Data
US 2016/0250069 A1    Sep. 1, 2016

(30) Foreign Application Priority Data

Nov. 15, 2013  (CH) ........................................ 1911/13
Dec. 17, 2013  (CH) ........................................ 2084/13

(51) Int. Cl.
*A61F 2/16*     (2006.01)
*A61F 9/00*     (2006.01)
(52) U.S. Cl.
CPC .......... *A61F 9/0017* (2013.01); *A61F 2/1678* (2013.01)

(58) Field of Classification Search
CPC ............................. A61F 9/0017; A61F 2/1678
(Continued)

(56) References Cited

U.S. PATENT DOCUMENTS 4,681,102 A * 7/1987 Bartell ................. A61F 2/1678
606/1
5,494,484 A * 2/1996 Feingold ................. A61F 2/167
206/5.1
(Continued)

FOREIGN PATENT DOCUMENTS

EP      1290990 A1    3/2003
EP      1905386 A1    4/2008
(Continued)

*Primary Examiner* — Amy R Weisberg
(74) *Attorney, Agent, or Firm* — Morriss O'Bryant Compagni Cannon, PLLC

(57) ABSTRACT

The invention relates to a device for receiving an intraocular lens, comprising a first and a second half-shell which are connected to each other in an articulated manner by a first joint and which can be moved relative to each other from an open position into a closed position. The half-shells form an open chamber in the open position and an enclosed chamber in the closed position. A covering element is pivotally arranged on the longitudinal side of the first of the two half-shells covering the open chamber in the open position and being positioned substantially outside of the enclosed chamber in the closed position. A movable or pivotal stopper can be provided which delimits the open chamber in the ejection direction of the lens in the open position and is positioned substantially outside of the enclosed chamber laterally to the ejection passage in the closed position.

20 Claims, 10 Drawing Sheets

(58) Field of Classification Search
USPC .................................................. 623/6.12
See application file for complete search history.

(56) References Cited

U.S. PATENT DOCUMENTS

| | | | | |
|---|---|---|---|---|
| 5,496,328 A * | 3/1996 | Nakajima | ............. | A61F 2/1678 606/107 |
| 5,499,987 A * | 3/1996 | Feingold | ............. | A61F 2/1664 206/5.1 |
| 5,582,614 A | 12/1996 | Feingold | | |
| 5,776,138 A * | 7/1998 | Vidal | ............. | A61F 2/1664 606/107 |
| 5,800,442 A * | 9/1998 | Wolf | ............. | A61F 2/167 606/107 |
| 5,803,925 A * | 9/1998 | Yang | ............. | A61F 2/1664 606/107 |
| 5,810,833 A * | 9/1998 | Brady | ............. | A61F 2/1664 606/107 |
| 5,810,834 A * | 9/1998 | Heyman | ............. | A61F 2/1678 606/107 |
| 5,876,440 A * | 3/1999 | Feingold | ............. | A61F 2/1664 128/898 |
| 5,941,886 A * | 8/1999 | Feingold | ............. | A61F 2/1664 606/107 |
| 5,947,975 A * | 9/1999 | Kikuchi | ............. | A61F 2/1664 606/107 |
| 6,001,107 A * | 12/1999 | Feingold | ............. | A61F 2/1664 206/5.1 |
| 6,179,843 B1 * | 1/2001 | Weiler | ............. | A61F 2/1662 606/107 |
| 6,248,111 B1 * | 6/2001 | Glick | ............. | A61F 2/1675 606/107 |
| 6,267,768 B1 * | 7/2001 | Deacon | ............. | A61F 2/1664 606/107 |
| 6,283,975 B1 * | 9/2001 | Glick | ............. | A61F 2/1675 606/107 |
| 6,355,046 B2 | 3/2002 | Kikuchi et al. | | |
| 6,447,520 B1 * | 9/2002 | Ott | ............. | A61F 2/1678 606/107 |
| 6,712,848 B1 * | 3/2004 | Wolf | ............. | A61F 2/1678 606/107 |
| 7,892,282 B2 * | 2/2011 | Shepherd | ............. | A61F 2/1667 606/107 |
| 7,892,283 B2 * | 2/2011 | Shepherd | ............. | A61F 2/1667 606/107 |
| 8,740,977 B2 * | 6/2014 | Niwa | ............. | A61F 2/167 606/107 |
| 2002/0193805 A1 * | 12/2002 | Ott | ............. | A61F 9/0017 606/107 |
| 2003/0036765 A1 * | 2/2003 | Van Noy | ............. | A61F 2/1678 606/107 |
| 2003/0195522 A1 * | 10/2003 | McNicholas | ............. | A61F 2/1678 606/107 |
| 2003/0216745 A1 * | 11/2003 | Brady | ............. | A61F 2/1678 606/103 |
| 2004/0087963 A1 * | 5/2004 | Ossipov | ............. | A61F 2/1675 606/107 |
| 2004/0199174 A1 | 10/2004 | Herberger et al. | | |
| 2004/0267359 A1 * | 12/2004 | Makker | ............. | A61F 2/1664 623/6.12 |
| 2005/0075646 A1 * | 4/2005 | Ohno | ............. | A61F 2/1678 606/107 |
| 2005/0125000 A1 * | 6/2005 | Tourrette | ............. | A61F 2/1678 606/107 |
| 2007/0005135 A1 * | 1/2007 | Makker | ............. | A61F 2/167 623/6.12 |
| 2008/0119864 A1 * | 5/2008 | Deinzer | ............. | A61F 2/1678 606/107 |
| 2008/0221584 A1 * | 9/2008 | Downer | ............. | A61F 2/1678 606/107 |
| 2009/0292294 A1 * | 11/2009 | Tanaka | ............. | A61F 2/1678 606/107 |
| 2010/0130985 A1 * | 5/2010 | Tanaka | ............. | A61F 2/1678 606/107 |
| 2011/0213380 A1 * | 9/2011 | Han | ............. | A61F 2/167 606/107 |
| 2011/0295264 A1 * | 12/2011 | Cole | ............. | A61F 2/1662 606/107 |
| 2011/0313425 A1 * | 12/2011 | Han | ............. | A61F 2/1678 606/107 |
| 2012/0016374 A1 * | 1/2012 | Han | ............. | A61F 2/1678 606/107 |
| 2012/0022547 A1 * | 1/2012 | Hildebrand | ............. | A61F 2/1672 606/107 |
| 2012/0130390 A1 * | 5/2012 | Davies | ............. | A61F 2/1691 606/107 |
| 2013/0012956 A1 * | 1/2013 | Mirlay | ............. | A61F 2/167 606/107 |
| 2013/0060256 A1 * | 3/2013 | Han | ............. | A61F 2/167 606/107 |
| 2013/0165943 A1 * | 6/2013 | Downer | ............. | A61F 2/1678 606/107 |
| 2014/0066946 A1 * | 3/2014 | Aguilera | ............. | A61F 2/1662 606/107 |
| 2014/0135784 A1 * | 5/2014 | Maroscheck | ............. | A61F 2/1678 606/107 |
| 2014/0303636 A1 * | 10/2014 | Valle | ............. | A61F 9/007 606/107 |
| 2015/0157500 A1 * | 6/2015 | Midorikawa | ............. | A61F 2/167 606/107 |
| 2015/0272779 A1 * | 10/2015 | Wagner | ............. | A61F 2/167 606/107 |
| 2015/0313709 A1 * | 11/2015 | Kobayashi | ............. | A61F 2/167 606/107 |
| 2015/0327992 A1 * | 11/2015 | Wagner | ............. | A61F 2/1678 606/107 |
| 2016/0074155 A1 * | 3/2016 | Raquin | ............. | A61F 2/1678 606/107 |
| 2016/0074156 A1 * | 3/2016 | Raquin | ............. | A61F 2/1678 606/107 |
| 2016/0151150 A1 * | 6/2016 | Sato | ............. | A61F 2/167 623/6.12 |
| 2016/0175090 A1 * | 6/2016 | Kobayashi | ............. | A61F 2/167 606/107 |
| 2016/0250069 A1 * | 9/2016 | Dockhom | ............. | A61F 2/1678 606/107 |
| 2016/0278914 A1 * | 9/2016 | Sato | ............. | A61F 2/1675 |
| 2016/0331587 A1 * | 11/2016 | Yamada | ............. | A61F 9/0017 |
| 2017/0128195 A1 * | 5/2017 | Helmy | ............. | A61F 2/1675 |

FOREIGN PATENT DOCUMENTS

| | | |
|---|---|---|
| EP | 2286762 A1 | 2/2011 |
| FR | 2892920 A1 | 5/2007 |
| JP | 2006068440 A | 3/2006 |
| WO | WO2003044946 | 5/2003 |
| WO | WO2003045285 | 6/2003 |
| WO | WO 2008098384 A2 * | 8/2008 ........... A61F 2/1678 |
| WO | WO2008098384 A2 | 8/2008 |

* cited by examiner (b)

(a)

DEVICE FOR RECEIVING AN INTRAOCULAR LENS, AND METHOD FOR FOLDING AN INTRAOCULAR LENS

CROSS-REFERENCE TO RELATED APPLICATIONS

This application is a national phase entry under 35 U.S.C. § 371 of PCT/CH2014/000166 filed Nov. 17, 2014, which claims priority to Swiss Patent Application No. 1911/131 filed Nov. 15, 2013 and Swiss Patent Application 2084/13 filed on Dec. 17, 2013, the entirety of each of which is incorporated by this reference.

TECHNICAL FIELD OF THE INVENTION

The present invention relates to a device for receiving an intraocular lens, and a method for folding an intraocular lens.

BACKGROUND OF THE INVENTION

In modern cataract surgeries, artificial lenses, so-called intraocular lenses, are standardly used in the capsular bag of the eye.

During the operation, an ocular incision of typically 2 to 4 mm is made, through which the natural lens is first removed and the implant is then inserted. For insertion, the artificial lens is introduced in a folded state through the incision in the capsular bag. Once the folded lens is inserted into the capsular bag, it unfolds back to its original shape The artificial lenses which are presently common comprise an optical lens body and two or more peripherally extending haptics which are transverse to the optical axis of the lens body, said haptics serving as position springs for the lens body within the capsular bag. For example, two haptics, which are arranged opposite one another on the lens body, extend in the same helical manner from the lens body.

Improved surgical tools and implants enable the surgeon to make visibly smaller incisions. The removal of the natural lens can presently be carried out through an incision of less than 2 mm. However, this only makes sense if the intraocular lens can be inserted through a similarly small incision.

For the insertion of intraocular lenses have been developed in recent years lens carriers or cartridges, in which a lens can be loaded and then ejected from the lens carrier by means of an injector.

Examples of such lens carriers or cartridges and injectors are known, for example, from patents U.S. Pat. Nos. 6,267,768, 5,810,833, 6,283,975, 6,248,111, 4,681,102, 5,582,614, 5,499,987, 5,947,975, 6,355,046 and EP 1 290 990 B1, as well as the disclosures US 2004/0199174 A1, EP 1 905 386 A1 and WO 03/045285 A1.

In the injector device according to U.S. Pat. No. 4,681,102, the cartridge which is formed as the folding device for the lens and the injector nozzle are separate parts. The cartridge can be inserted into the injector, whereupon the injector nozzle can be screwed onto the front of the injector housing.

In the injector device according to U.S. Pat. No. 5,582,614 and most known injector devices, such as U.S. Pat. Nos. 6,267,768, 5,810,833, 6,283,975 and U.S. Pat. No. 6,248,111, the cartridge is integrally formed from a folding device and an injector nozzle.

Intraocular lenses are sterile packed by the manufacturer and, if appropriate, come in a liquid bath. Depending on the lens material, storage in a liquid may be necessary to protect the lens from drying out. During surgery, the lens must be removed from the packaging in a sterile field and inserted or loaded into a cartridge or directly into an injector. Because these lenses represent very small and elastic structures, the risk exists when loading the cartridge or the injector that the lens is dropped or springs away during folding, thus losing its sterility. In addition, the lenses are very delicate structures which can easily be damaged during folding, injecting and reloading in a cartridge. The risk of damage is especially large for the so-called haptic which surrounds the optical portion of the lens. It is also possible that the optical part is damaged, for example by the forceps during insertion into the cartridge. These risks are particularly large in the cartridge according to U.S. Pat. No. 4,681,102, which provides no measures for detecting the lens edges during folding. In contrast, U.S. Pat. No. 5,582,614 proposes the introduction of grooves in the free ends of the half-shells of the cartridge, said grooves detecting the lens edges during folding of the lens. U.S. Pat. No. 5,499,987 provides grooves in a specific embodiment. Specifically, it is proposed that the groove be formed less deeply toward the nozzle, so as to facilitate transport into the nozzle (FIGS. 34, 39, 40 and 41 in U.S. Pat. No. 5,499,987). It is, however, disadvantageous that cartridges with such grooves cannot securely grasp the lens edges if the lens has a relatively large diameter and the cartridge for the insertion of the lens must be opened widely, i.e. a large opening angle exists. This disadvantage is not present in the cartridge according to U.S. Pat. No. 5,947,975 or U.S. Pat. No. 6,355,046, as it possesses two hinges, so that a different folding geometry arises than that of cartridges with a single hinge. It is, however, disadvantageous that for each lens size, a cartridge corresponding to this sized is needed. A further disadvantage is that the folding of the lens is not optimal (FIG. 11 and FIG. 15 in U.S. Pat. No. 5,947,975 or U.S. Pat. No. 6,355,046), so that the diameter of the injector tip must be kept relatively large. For this reason, an undesirably large ocular incision is also necessary to insert the lens into the capsular bag of the eye.

As shown in EP 1 290 990 B1, WO 03/045285 A1 and EP 1 905 386 A1, this cartridge construction continued to be maintained in later years, said cartridge construction comprising two half-shells connected by a single hinge, whether with or without grooves or holding devices for grasping the lens edges.

The disclosure of WO 03/045285 A1, for example, shows a method for inserting an intraocular lens in the capsular bag of the eye in which an overpressure is generated in order to eject a loaded lens floating in a lubricant from the injector nozzle. a compressible and deformable piston continuously adapts itself to the forward-tapering nozzle channel. Along the way the lens is further folded and at the end of its journey has a very small diameter. Due to the deformability of the piston, the end of the nozzle channel may be kept very narrow, hence only a very small incision is necessary. A kit for carrying out the method contains a lens carrier and a lens. The lens is located on the lens carrier in a tensionless state. The lens and lens carrier may be supported by a holder and sterile packed in a package until use, and in the case of a hydrophilic lens, specifically in a liquid which protects the lens from drying out. During the operation, the lens carrier along with the lens supported therein are removed from the packaging, inserted into the injector and folded. A lubricating liquid is filled thereupon through the channel. The lens can then be injected into the capsular bag of the eye to be treated.

Because cartridges with ridges for grasping the lens edges are unsatisfactory during folding, a cartridge is proposed in US 2004/0199174 which likewise comprises two half-shells in the conventional manner. Therein is shown in particular an injector device in which the injector housing consists of a cylinder for receiving the piston, a folding device for the lens and an injector nozzle. In addition is provided a flexible elastic band, which leads from the first half-shell to the second half-shell and which can be pulled through a slot on the edge thereof. An intraocular lens is inserted between a loop of the band, and the half-shells. By pulling on the band, the half-shells can be moved toward each other, and the lens (which extends unfolded beyond the edges of the half-shells) is pressed into the half-shells, so that the intraocular lens is thereby folded. During folding, the lens is thus held by the band. The band acts as a folding aid. Disadvantageous is the complicated design of the cartridge and the complicated handling thereof. In addition, the haptics can be pinched, for example, between the band and the slot.

There are preloaded systems. These have already been loaded at the factory with a lens in the unfolded state (so-called preloaded systems), so that the previous delicate loading operation is no longer necessary before the operation. The surgeon need only undertake the folding process and introduce the lubricating liquid. Holders are known for preloaded systems which hold a preloaded lens during transport into its storage position. These holders are removed or fall off during folding of the lens, before the lens can be injected into an eye. The removal of a holder constitutes an additional manipulation step. A part which falls off may have a disruptive effect; for example, it must be collected and removed from the surgical area.

In general, systems for prefolded lenses and systems for lenses which are not prefolded can be distinguished in the prior art. In the systems without prefolded lenses, the lenses are folded only during the process of insertion for the injection. In particular, systems are used for this purpose in which the lens is loaded from the back into a loading chamber in a still unformed or unfolded state (as is shown for example in U.S. Pat. No. 5,810,833). Systems for lenses which are not prefolded disadvantageously require relatively large incisions, because during the process of insertion, a folding which is as small as desirable cannot occur for various reasons. In the systems with prefolded lenses, the lenses are folded or prefolded before the process of insertion for the injection. Winged cartridges are used in particular for this purpose (such as disclosed in U.S. Pat. Nos. 6,267,768, 6,248,111, 5,947,975 or U.S. Pat. No. 4,681,102). The lens is folded during closing of the winged cartridge and is present in a prefolded state in the loading chamber. Systems with winged cartridges advantageously require only small incisions. It is disadvantageous that the lens, in particular the haptic, can be pinched during insertion or folding, or the haptic can assume an unfavorable position during this process.

None of the previously mentioned documents disclose a system which can always be manipulated without failure and/or in which the risk that the haptic of the lens is pinched during folding is completely eliminated. A pinched or disadvantageously trapped haptic may break, at the latest, during injection of the lens. If many manipulation steps are necessary to prepare the lens and injector, this can represent a corresponding number of sources for error.

Advantages

It is therefore an advantage of the present invention to provide a device for easily loading an intraocular lens, which avoids the disadvantages of the described known systems and methods. In addition, a device is to be provided which folds an intraocular lens without damage during folding and/or injection and which is suitable for use with small incisions. In addition, an apparatus is to be provided which is optimized with regard to the manipulation steps for preparation of the lens and injector. In particular, as few manipulation steps as possible should be necessary which must be carried out on the device after delivery of the lens and injector and directly before the surgical procedure. Sources of error are thereby to be reduced. A further advantage is to provide a device which requires only small incisions in the eye during use.

These and other advantages are achieved by the features of the independent claims. Further developments and/or advantageous embodiments of the invention are subjects of the dependent claims.

SUMMARY OF THE INVENTION

The advanatages are achieved according to the invention by a device for receiving an intraocular lens, comprising a first and a second half-shell which are connected to each other in an articulated manner by a first joint and which can be moved relative to each other from an open position into a closed position, wherein the half-shells form an open chamber in the open position and an enclosed chamber in the closed position and wherein, according to the invention, a covering element is pivotally arranged on the longitudinal side of the first of the two half-shells, said covering element bounding, in particular covering or spanning, the open chamber in the open position and being situated or positioned outside (or substantially outside) of the enclosed chamber in the closed position, in particular between the two half-shells. The covering element is (and may remain) arranged on the first half-shell or connected with the first half-shell, both in the open position and the closed position.

The device according to the invention is advantageously designed as a cartridge for insertion into an injector housing. Alternatively, the device according to the invention may be an integrated part of an injector.

Pinching of the lens, and in particular the haptic thereof, during closing of the half-shells can be avoided with the aforementioned device. During use of the device according to the invention, the user can visually recognize where the lens is positioned in the device or cartridge according to the invention. The initial position of the lens before the folding process can thus be checked visually. Incorrect placement of the lens can be ruled out. Accordingly, the covering element also acts as a positioning aid and a cover during storage and preparation of the lens.

The inventive device can be used with a relatively small incision on the eye (in particular in incisions with a diameter of less than 2.5 mm, or less than 2.2 mm, or less than 2 mm, or than 1.5 mm). This is achieved because the device according to the invention comprises a loading chamber for a folded lens to be injected, said loading chamber being enclosed in a jacket-like manner and thus (longitudinally) closed. The lens is prefolded therein to a particularly small cross-sectional diameter, and can be injected by means of a narrow cannula and through—as described—a particularly small incision. Said device is particularly advantageously used with a deformable pusher, particularly a silicon pusher (e.g. according to the disclosure WO 03/045285 A1).

The advantageous features embodied below lead individually and in combination with one another to further improvements of the device according to the invention and its use.

Pivotally arranged may mean that the covering element is integrally formed on the first half-shell. From a manufacturing standpoint, it is particularly advantageous if the covering element is integrally formed with the first half-shell and optionally further together with the second half-shell. A one-piece cartridge can, for example, be produced inexpensively by injection molding.

The covering element is in particular pivotable such that it is functionally self-supporting, rigid and/or plate-shaped.

Advantageously, at least the first half-shell and the covering element, such as the first half-shell, the second half-shell and the covering element are non-detachably connected to one another; i.e. cannot be separated under conditions of normal use. Here, normal use includes in particular loading, storage, folding and ejecting or injecting of a lens.

According to the invention, the covering element is pivotally arranged in particular on the longitudinal edge of the first half-shell, i.e. on the longitudinal side of the half-shell facing away from the first joint.

The covering element is functionally connected with the first half-shell via a second joint, which is formed, for example, as a hinge, in particular as a film hinge. The covering element is in particular pivotable about the second joint.

A bending groove may be formed on the covering element surface which turns away the inner surface of the first half-shell.

For stabilizing the device in the open position, it is advantageous if a covering element support, such as with an engagement groove, is provided on the longitudinal edge of the second half-shell.

Optionally, each half-shell is equipped with a support. The support may be formed, for example, in the form of at least one slide rail.

The device is advantageously configured such that upon closing of the two half-shells, the covering element slides over the longitudinal edge of the second half-shell out of the closing chamber.

To ensure proper function as a loading channel, the closed chamber forms a channel in the closed position of the half-shells, in particular a cylindrical loading channel. Each of the half-shells thereby advantageously forms a cylindrical segment.

For better handling, wings (i.e. wing handles) are arranged on both half-shells, in particular on the longitudinal edge of the half shells.

It may be advantageous if a closure, in particular a snap closure, is formed on the wings.

In the closed position of the half-shells according to the invention, the covering element is arranged outside (or substantially outside) the enclosed chamber, it may be located (at least partially) between the edges of the half-shells or (substantially) between the wings (or between the edges of the half-shells, which are formed as wings), it may optionally be clamped between the edges or the wings.

The covering element may be self-supporting or stably formed, in particular as a small plate. The covering element is in particular dimensionally stable or self-supporting under conditions of normal use. Here, normal use of the device includes in particular loading, storage, folding and ejecting or injecting of a lens. The covering element is thus not flexible under normal use, i.e. it does not flex, therefore does not deform significantly, and behaves substantially rigidly. The covering element is thereby in particular pivotable about the second joint. A band (which is flexible by definition) is not suitable as a covering element.

The covering element may comprise an opening, which is used to fill the still-open chamber and optionally the injector nozzle with lubricant.

It is useful if the covering element comprises a stopper for the lens. The stopper may be arranged, in particular integrally formed, at the front side of the device or at the front side of the cartridge on the covering element. Functionally advantageously, the lens including the front haptic thereof are prevented by means of the stopper from exiting from the front and possibly falling out of the device. Furthermore, the front haptic can be placed against the optic by means of this stopper when the lens is pushed forward against the stopper. A better exit behavior of the lens hereby results.

It may in particular be useful if the covering element comprises two stoppers, i.e. a first stopper and a second stopper, the first stopper (as indicated above) for bounding the front haptic and the second stopper for bounding the rear haptic. This embodiment with two stoppers is particularly advantageous in that a lens stored in liquid, which is preloaded in a device according to the invention, which is formed as a cartridge, can be removed from the storage container and inserted into the injector such that the lens cannot thereby fall out of one of the two sides of the cartridge (i.e. the front end side or the rear end side of the cartridge).

Advantageously, the covering element is shortened in the longitudinal direction with respect to the half-shells, and may be shortened and stepped or shortened and slotted.

In accordance with the injector housing, a plug device can be formed on one of the half-shells for inserting into a receiving opening of the injector housing. The plug device may be provided on the second half-shell.

From a manufacturing perspective, it is advantageous if the device is integrally formed and and may comprise plastic. Injection molding may be used in this case.

In addition is disclosed herein an injector with an injector housing and a plunger for use with a device which is formed as a cartridge as described above, said plunger being displaceable in a longitudinal direction in the injector housing.

According to the invention, the above advantages achieved by a method for folding an intraocular lens which comprises the following steps:

Providing a cavity, the outer shell of which comprises a first half-shell, a second half-shell and a covering element, wherein the first half-shell is connected in an articulated manner on one side via a first joint with the second half-shell and connected in an articulated manner on the opposite side via a second joint with a covering element, wherein the covering element is slidably in contact with the (free) edge of the second half-shell, Inserting a lens into the cavity, where the entire lens body (41) of the lens (33) is introduced into the cavity, Bringing together the two half-shells via the first joint, where the side of the first half-shell with the covering element is brought to the edge of the second half-shell through rotation about the first joint, wherein simultaneously the covering element slides over the edge of the second half-shell out of a cavity forming between the two closing half-shells, which means simultaneously a rotation of the covering element about the second joint. The covering element slides in particular between two wings, which are each formed or integrally formed on one of the half-shells.

The aforementioned outer shell is in three pieces or comprises three pieces, a first half-shell, a second half-shell and a covering element. Here, the three elements or parts may be integral parts of a single injection molded part.

At least one haptic of the lens may be pushed toward the lens body. In particular, the front haptic of the lens is pushed toward the lens body by means of a stopper. In the presence of a front stopper, the front haptic can be pressed against the lens body under the plunger pressure on the lens. It may further be advantageous to push the rear haptic of the lens toward the lens body directly via a stopper (i.e. by means of a stopper), in particular a flexible stopper. In this way, the haptics are prefolded.

It is advantageous that the lens can be inserted into the cavity in an untensioned state. This means that the lens can be inserted (in particular by hand) into the device without externally applied mechanical tension, in particular without bending or folding of the lens.

Functionally advantageously, the lens is supported—particularly after insertion by hand—(at least partially) on the inner surfaces of the two half-shells. This means that the lens is supported at least on one point on the inner surface of each half-shell.

Functionally, the lens is grasped at its edges by the two half-shells and is folded together along with the half-shells (e.g., in approximately the same direction). During the folding process, the covering element is not in contact with and does not touch the lens. The covering element does not act on the lens during folding, and is therefore not a folding aid.

In the process of being brought together, the two half-shells may be brought together until they contact one another or until the two longitudinal edges of the two half-shells contact one another, wherein the covering element is clamped. The covering element may be clamped between the two longitudinal edges. The edges are advantageously outfitted with wings, which in the closed position of the half-shells clamp, and thereby secure and fix, the covering element. It is ensured that the covering element is slid out of the closing chamber and simultaneously fixed outside the closing chamber, in particular between the edges of the half-shells such as between the wings, such that, during subsequent ejecting of the lens, the covering element does not obstruct the ejection of the lens, for example for injection into an eye, either inside of the enclosed chamber or outside thereof. During pivoting, the pivotable covering element may slide along the second wing and out of the forming closing half-shells.

Furthermore is disclosed an alternative device for receiving an intraocular lens, comprising a first and a second half-shell which are connected to each other in an articulated manner by a first joint and which can be moved relative to each other from an open position into a closed position, wherein the half-shells form an open chamber in the open position which serves for the insertion of the lens, and an enclosed chamber in the closed position which forms an ejection passage and serves to eject the lens, said device being at least characterized according to the invention in that at least one stopper (or stopper element) is displaceably or pivotally arranged on the first of the two half-shells, said stopper bounding the open chamber in the direction of ejection in the open position and being positioned outside (or substantially outside) of the enclosed chamber lateral to the ejection passage in the closed position. During the fitting of the device with a lens, the stopper helps to correctly position the lens and the haptic thereof.

This device can be combined with the features as defined above, insofar as the features are not mutually exclusive. In particular, the feature of a covering element may be present in combination with the at least one stopper.

The stopper (or the stopper element) is functionally formed on a holding element, for example the covering element or an arm, wherein the holding element functionally bridges or spans the open chamber in the open position and is positioned (substantially) outside the enclosed chamber in the closed position.

It is advantageous that the holding element be displaceably or pivotally arranged on the longitudinal edge of the first half-shell. By this displaceable or pivotable arrangement of the holding element, it is effected that the stopper (i.e. the stopper element) is displaceable or pivotable.

The displaceable or pivotable arrangement of the stopper and the holding element results in particular in that the stopper and the holding element are connected with the first half-shell via a second joint, which is formed, for example, as a hinge, in particular a film hinge. The second joint (in particular a hinge or film hinge) results in particular from the formation of a bending groove on the side of the holding element turning away the inner surface of the first half-shell.

A holding element support, in particular with an engagement groove, may be formed on the longitudinal edge of the second half-shell.

The device is in particular formed such that upon closing of the two half-shells, the holding element slides over the longitudinal edge of the second half-shell out of the closing chamber.

For better operation of the device, wings are arranged on both half-shells, in particular on the longitudinal edge of the half-shells. A closure, in particular a snap closure, may be formed on the wings.

In the closed position, the holding element is (substantially) positioned outside the enclosed chamber and may lie between the wings.

The holding element is in particular formed to be self-supporting.

Optionally, a plurality of holding elements, in particular for example two arms, may be present, wherein each holding element or each arm supports at least one stopper, meaning, for example, a first stopper on a first, front arm for preventing the sliding of the lens or the haptic thereof out of the open chamber to the front, and a second stopper on a second, rear arm for preventing the sliding of the lens or the haptic thereof out of the open chamber to the back, in particular a first stopper for the first or front haptic of the lens and a second stopper for the second or rear haptic of the lens.

Advantageously, the holding element is an integral part of the device and/or is made of plastic. The inventive device can be manufactured in one piece through injection molding.

It is functionally advantageous if each half-shell is equipped with a support, formed, for instance, as slide rails.

In the closed position of the half-shells, the enclosed chamber forms a channel, in particular a loading chamber.

On the device, a plug device can be formed on one of the half-shells for inserting into a receiving opening of an injector housing.

The alternative device presented here is suited as, or is in particularly formed as, a cartridge for use in an injector, in particular an injector housing. Thus is further disclosed an injector with an injector housing and a plunger for use with a device which is formed as a cartridge as described herein, said plunger being displaceable in a longitudinal direction in the injector housing.

Further disclosed herein is an additional method for folding an intraocular lens comprising the steps:

Providing a loading surface, which is defined at least by a first half-shell and a second half-shell, and a holding element with a stopper (i.e. stopper element), said holding element spanning the first and second half-shells, wherein the first half-shell is connected in an articulated manner on one side via a first joint with the second half-shell and connected in an articulated manner on the opposite side via a second joint with the holding element, wherein the holding element is slidably in contact with the longitudinal edge of the second half-shell, Applying (in particular laying or pushing) a lens onto the loading surface, in that the entire lens body of the lens is placed on the loading surface, Bringing together the two half-shells via the first joint, where the side of the first half-shell with the holding element is brought to the edge of the second half-shell through rotation about the first joint, wherein simultaneously the holding element slides over the edge of the second half-shell out of a cavity forming between the two closing half-shells, which means simultaneously a rotation of the holding element (and thus the stopper) element about the second joint.

The method is in particular characterized in that, in the use of a lens with two haptics, the front haptic of the lens is or will be pushed toward the lens body via a stopper, and the rear haptic is or will be pushed toward the lens body via a plunger. Advantageously, the lens can be placed on or applied to the loading surface in an untensioned state. The lens is functionally supported on the inner surfaces of both half-shells. The lens is optionally grasped at its edges by the two half-shells and is folded together along with the half-shells (in particular in approximately the same direction). The process step of bringing together of the two half-shells comprises in particular a bringing together of the two half shells until they contact one another or until the two longitudinal edges of the two half-shells contact one another, wherein the holding element is clamped.

Additional advantages of the present invention will become apparent from the following description.

BRIEF DESCRIPTION OF THE FIGURES

Further embodiments of the invention will become apparent from the following description with reference to figures. Shown schematically, not to scale

DETAILED DESCRIPTION OF THE FIGURES

Figure 1:
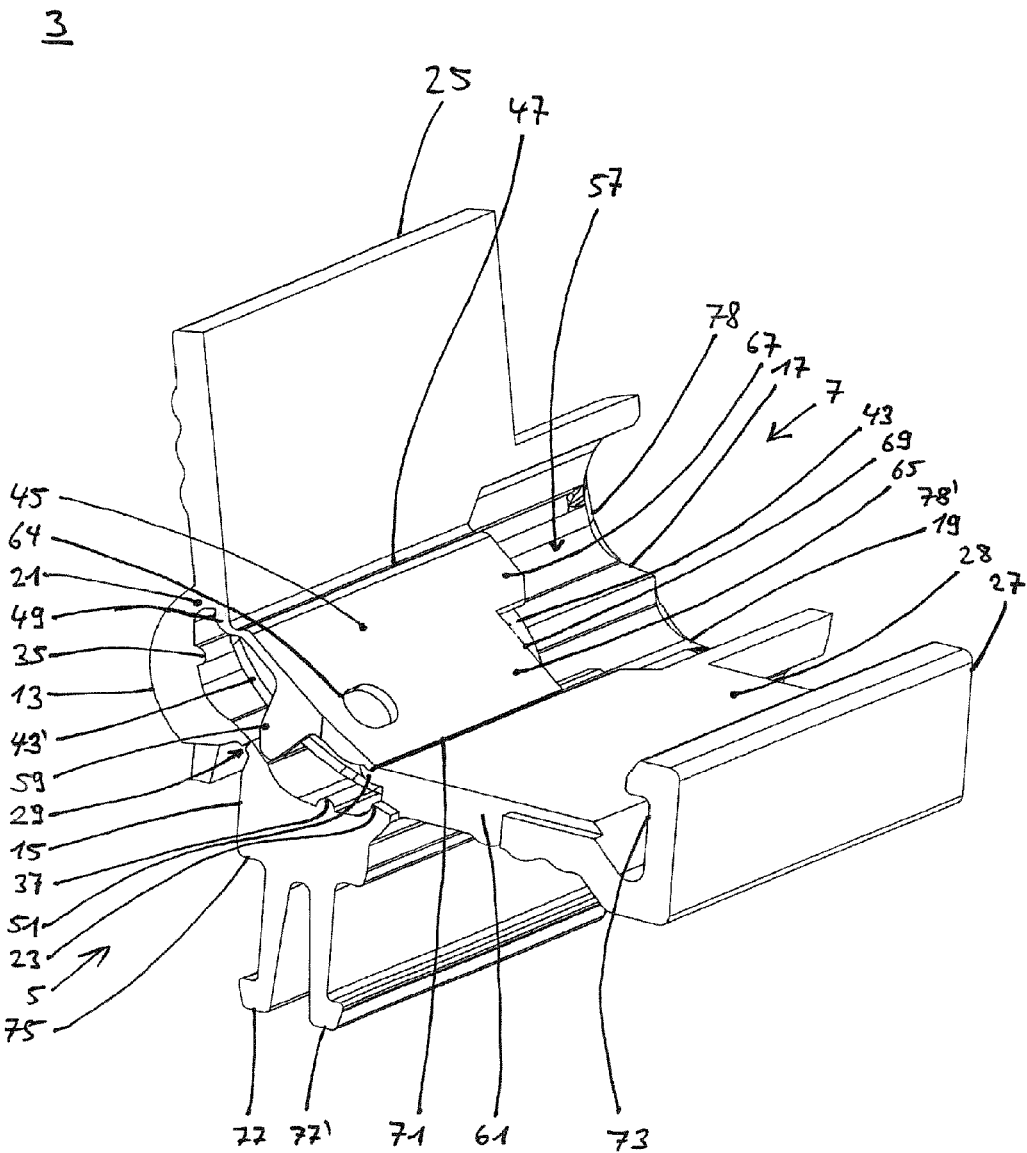
FIG. 1: shows an oblique view of the device according to the invention in the open position with loaded intraocular lens.

In the following, like reference characters represent identical or functionally identical elements (in different figures). The addition of an apostrophe may be used to distinguish between multiple identical, similar, functionally identical or functionally similar elements.

In FIGS. 1-4 is represented a device according to the invention in the form of a cartridge 3 which can be inserted into an injector housing 1. Alternatively, the device according to the invention may be part of an injector or be permanently integrated or fixed in the injector.

In FIGS. 6-9 is shown an injector with an inserted cartridge 3.

The injector is an operation tool with a sleeve-like housing 1 and an axially moveable plunger 9 received in the housing. An elastic pusher may be placed on the plunger 9. A recess, for example a slot, may be provided in the jacket of the housing, in which a lens carrier, i.e. in particular the cartridge 3 described herein, can be loaded. The lens carrier or the cartridge 3 may have a cylindrical loading channel 39, to which is axially connected an injector nozzle 11, which tapers in the direction of the tip (distal end of the lens carrier). The lens carrier or cartridge 3 is inserted and held in the injector housing 1 such that the plunger 9 is aligned with the loading channel. While advancing, the plunger 9 penetrates the loading channel 39 and pushes the lens out of the injector nozzle 11.

The cartridge 3 has a front end 5 and a rear end 7. Inserted into an injector 1, the plunger 9 can be pushed from the rear end 7 in and through the cartridge 3 in the direction of the front end 5 of the cartridge 3 and further into the injection cannula 11.

The cartridge 3 comprises two half-shells 13 and 15, which are connected to each other in an articulated manner via a first joint 29. The two half-shells 13 and 15 are in particular formed cylindrically segmented and longitudinally hinged together. The two half-shells 13 and 15, which are connected to each other in an articulated manner, together form a double half-shell. Each half-shell 13, 15 comprises on its inner side an open half channel with an inner surface 17 or 19. The inner surfaces 17 and 19 together form a loading surface 20. The loading surface 20 is bounded longitudinally by a first edge 21 and a second edge 23. In other words: each half-shell 13, 15 comprises an edge 21 or 23 on a side facing away from the first joint 29. On each edge 21, 23 is advantageously arranged a wing 25, 27. The half-shells 13 and 15 are connected to each other in an articulated manner in the longitudinal direction via the first joint 29, which is functionally designed, for example, as a hinge or film hinge. The two half-shells 13 and 15 are thereby juxtaposed in such a manner that the inner surfaces 17 and 19 of the two half-shells 13 and 15 adjoin one another, in particular are adjacent to one another in the longitudinal direction (or pass from one to the other via the first joint 29) and form a common loading surface 20. Longitudinal or longitudinal side means here in alignment along the extension or orientation of the half-channels. The cartridge 3 can be transferred from an open position to a closed position by virtue of the joint 29. In the open position (FIGS. 1 and 2), the two half-shells 13 and 15 form a type of loading surface 20, on which an intraocular lens 33 can be loaded and on which the lens can optionally be stored without tension. The lens 33 lies thereby between the longitudinal edges 21, 23, such as on a guiding structure, which here comprises, for example, slide rails 35, 37. During closing, the longitudinal edges 25 and 27 of the two half-shells 13 and 15 approach one another and an artificial intraocular lens 33 which is laid on the loading surface 20 is grasped and folded. In the closed position (FIGS. 3 and 4), the two half-shells 13 and 15 together form a closed channel, i.e. the above-mentioned loading channel 39, which serves to keep the lens 33 in a folded state ready for injection into an eye.

Figure 5A:
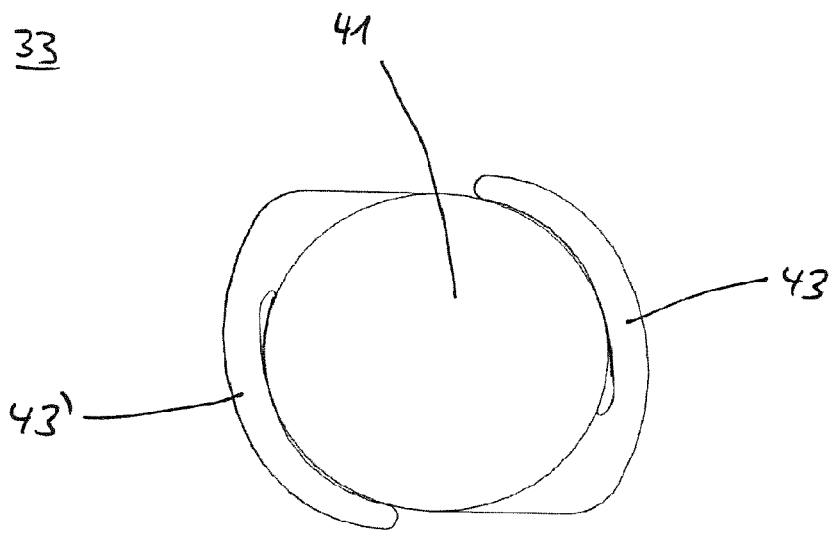
FIG. 5a: shows an optical lens with folded first and second or front and rear haptics.
Figure 5B:
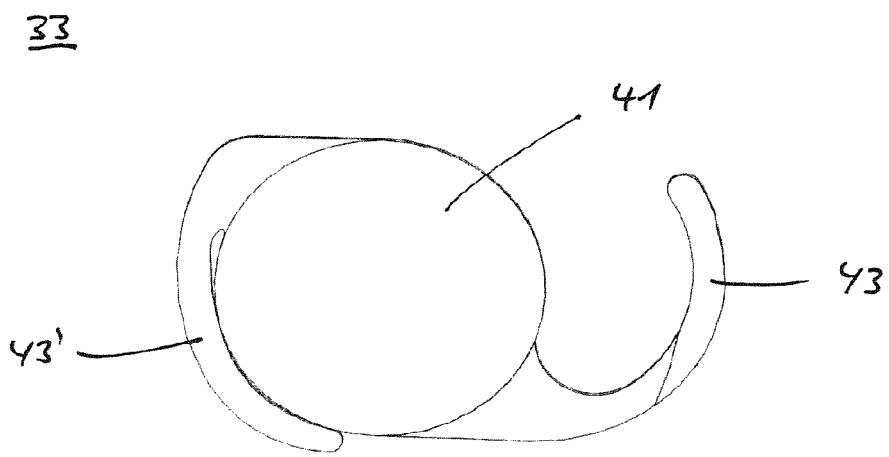
FIG. 5b: shows an optical lens with a first folded haptic and a second open haptic.

Intraocular lenses 33 substantially comprise an optical lens body 41 and one or more haptics 43, such as a first and a second haptic 43, 43' (FIG. 5), which usually extend flexibly from the periphery of the lens body 41 from the plane of the lens in a helical manner (in particular helically in the same direction). To avoid pinching of the lens 33 and in particular the haptic 43 thereof during closing of the half-shells, the cartridge 3 is outfitted according to the invention with a covering element 45.

The covering element 45 is movably, in particular displaceably or foldably (similar to a single-leaf swinging door), arranged or fixed on the longitudinal edge 21 of the first half-shell 13. The covering element 45 is advantageously formed as a covering plate, in particular as a flat, rigid covering plate. In an open position of the cartridge 3, the covering element 45 spans the loading surface 20 from the longitudinal edge 21 of the first half-shell 13 to the longitudinal edge 23 of the second half-shell 15.

The covering element 45 is advantageously movably fixed via a second joint 47 on the longitudinal edge 21 of the first half-shell 13. The joint 47 is functionally advantageously a hinge, in particular a film hinge, and is formed as a bending groove or seam area.

The axes of rotation of the first and second joints 29 and 47 are may be aligned parallel to each other.

Figure 3:
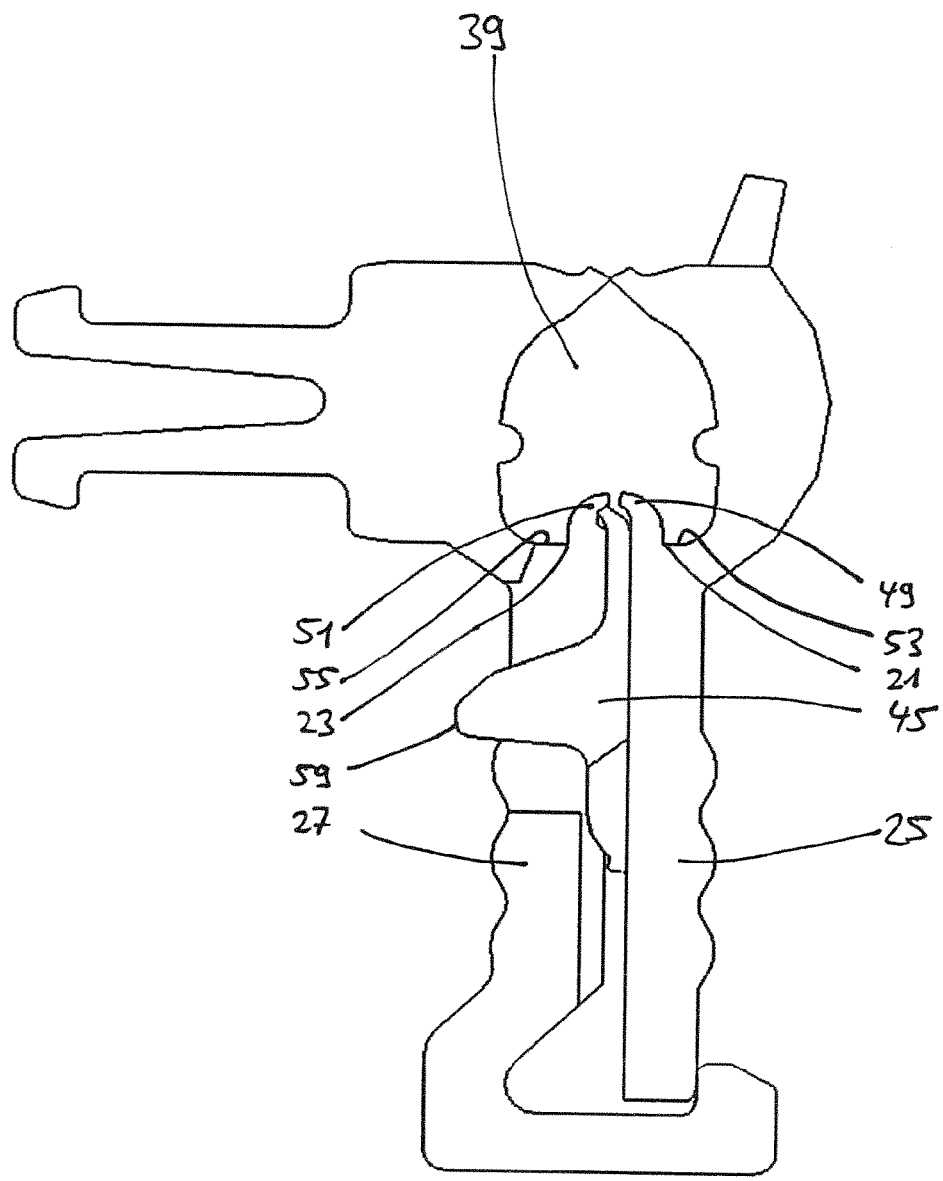
FIG. 3: shows a front view of the device according to the invention in the closed position.
Figure 4:
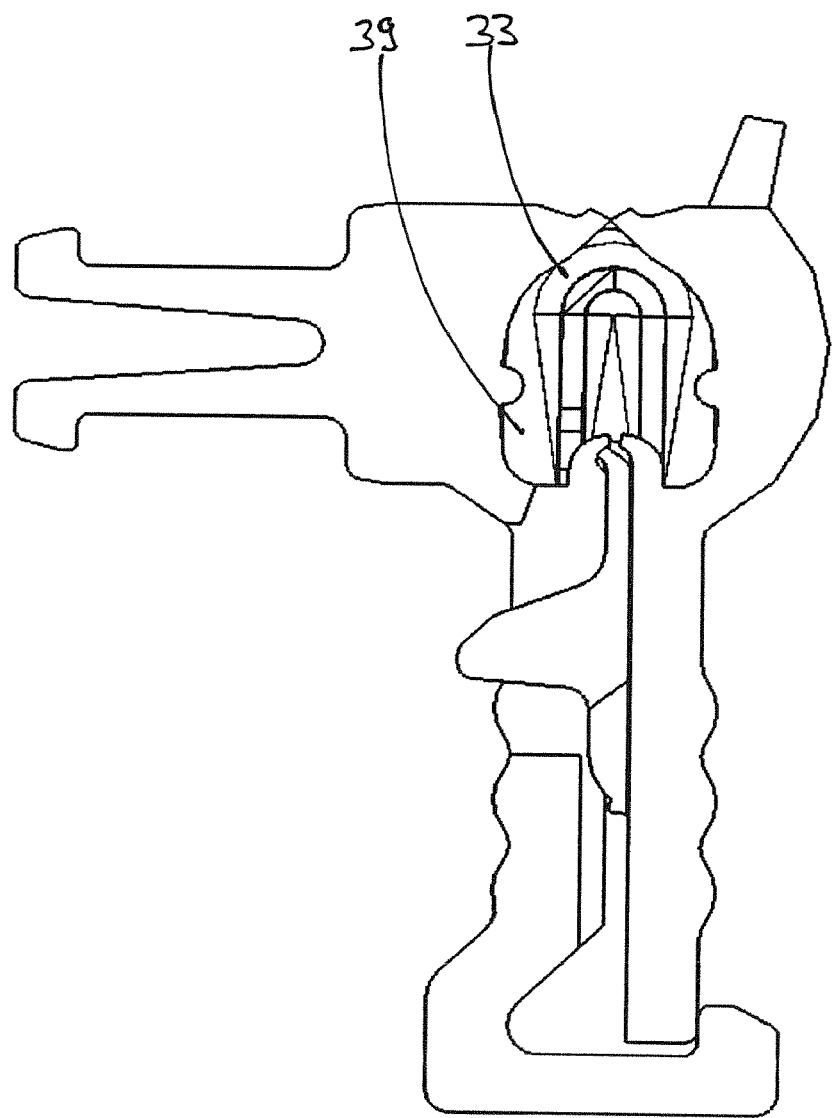
FIG. 4: shows a front view of the device according to the invention in the closed position with loaded intraocular lens.

The covering element 45 closes toward the longitudinal edge 23 due to the force of gravity and/or a spring force of the second joint 47. Because the covering element 45 is self-supporting (i.e. sufficiently stiff), the cartridge 3 forms in the open position a covered chamber 46 between the first half-shell 13, second half-shell 15 and covering element 45. The second joint 47 may be disposed on a strip 49 protruding from the longitudinal edge 21 of the first half-shell 13. On the opposite side, i.e. the longitudinal edge 23 of the second half-shell 15, a second protruding strip 51 may be formed, which serves as a support for the covering element 45 when the cartridge 3 is open. The strips 49 and 51 are both functionally advantageously curved and optionally formed with tapering ends or longitudinal sides. The tapered ends or the tapered longitudinal sides of the strip 49 functionally advantageously pass over to a film hinge. The curvature of the strips 49, 51 is in particular a camber along the length thereof. The curvature of the strips 49, 51 is formed such that in the closed cartridge, the two strips complete a semicircular bulge with one another, which extends into the closed channel 39. The strips 49, 51 form in longitudinal continuation of the inner surfaces 17, 19 a countersurface to the respective inner surface 17, 19 on the respective longitudinal edge 21, 23, wherein a type of inner indentation 53, 55 is formed on the respective longitudinal edge 21, 23 (FIG. 3). The indentations 53 and 55 and the slide rails 35 and 37 may interact as a guide system for the introduction of a lens 33. The strips 49, 51 may be formed continuously in the longitudinal direction (as shown in the figures) or discontinuously (not shown in the drawings). The guide system is functionally advantageously designed parallel to the longitudinal extension of the half-shells 13, 15.

External to the chamber, the strip 49 may be formed with a concave bending groove. The bending groove comprises in particular a linear displacement in the longitudinal direction of the first half-shell 13, whereby a bendability of the material is produced. The covering element 45 can thereby be folded toward the first wing 25 in an articulated manner. The bending groove functions in particular as a film hinge.

External to the chamber, the strip 51 may be provided with a concave groove 56. In a corresponding configuration of the free end 58 of the covering element 45, the free end 58 of the covering element 45 can engage in this groove 56. The groove 56 and free end 58 are formed such that when pressing (i.e. actuation by hand) the two wings 25, 27 shut, the covering element 45 or the free end 58 thereof are pushed out of the groove 56 and slide along the wing surface 28. For this purpose, the free end 58 of the covering element 45 is functionally advantageously outfitted with a tapering convex curve 60 on the inner side of the chamber, which may end with a bead-like seam 62. The strip 51 thus forms a type of covering element support 63 with engagement groove 56.

If the covering element 45 is formed in a shortened manner in the longitudinal direction with respect to the half-shells or the inner surfaces 17, 19 thereof, the free or uncovered part 57 of the loading surface 20 may serve as a depositing location for the lens 33, on which the lens may be deposited, for example by hand, before said lens is pushed along the loading surface 20 under the covering element 45.

So that a lens 33 which has been pushed from the depositing location 57 into the covered chamber 46 does not escape from the front end face 5 of the cartridge 3, the covering element 45 is equipped with a stopper 59. This also serves for the application of the distal haptic to the optic body of the lens. The stopper is applied on or near the front side of the cartridge 5, i.e. proximal on the cartridge. The stopper 59 may be formed as a protuberance which protrudes on the inner surface side (i.e. on the side of the inner surfaces 17, 19) from the plane of the covering element when the cartridge is open (in particular when the free end of the covering element 45 lies on the second edge 23 or on the second strip 51).

Functionally advantageously, the second wing 27 comprises a guide, for example a track or a recess 61 on the end face of the cartridge, in or along which the stopper 59 can slide, when the covering element 45 is guided over the second wing out of the forming chamber 39 during closing of the cartridge 3.

In the longitudinal direction of the half-shells 13, 15, the diameter of the wing 27 of the second half-shell 15 may be approximately corresponds to the diameter of the covering element 41, or extends beyond this.

The covering element 45 optionally comprises an opening 64. This may be located in the front region of the covering element 45 and optionally in a region of the covering element 45 which lies opposite the second inner surface 19 or—in other words—which abuts the second edge 23. In the longitudinal direction, the opening 64 is functionally advantageously spaced less than one half the diameter, such as less than one third the diameter, of a lens body 41 from the front end face 5 of the cartridge 3 or from the stopper 59.

Through this opening 64, lubricating liquid for the lens can be introduced, and in particular the front part of the cartridge 3, i.e. before the lens 33, and the injector nozzle 11 are thereby also filled with lubricating liquid. The lubricating liquid may, for example, be introduced after the lens has already been pushed under the covering element 45.

The covering element 45 is shortened at the rear part of the cartridge in the longitudinal direction with respect to the half-shells 13, 15, or shortened and stepped (FIG. 1 and FIGS. 6-8). In particular, the covering element 45 is shortened with respect to the half-shells 13, 15 in a rear region 65 of the covering element which is primarily opposite to the second inner surface 19 or—in other words—which abuts the second edge 23. In a rear region 67 of the covering element 45 which is opposite the inner surface 17 or—in other words—which abuts the first edge 21, the covering element 45 may likewise be shortened with respect to the half-shells 13, 15, however this need not necessarily be the case. In said region 67 over the first inner surface 17, the covering element 45 may be less shortened than in the region 65 over the second inner surface 19. In particular, the region 65 of the covering element, which is adjacent to the free end of the covering element, is thus more strongly shortened with respect to the length of the cartridge 3 than the region 67 which is adjacent to the second joint 47. Due to the shortening, a one-sided recess may be produced in the rear part of the covering element 45, in which a plunger 9 of an injector can be pushed up to the stop 69 and thus up to an inserted lens 33, if necessary the lens body 41, without necessitating the lifting or otherwise displacing of the covering element 45. The width of the covering element region 67 is dimensioned such that, in the closing process of the cartridge 3, the covering element region 67 slips over the plunger 9, which has been pre-pushed up to the stop 69 of the recess, without the free end 71 (in particular the seam 62) of the covering element 45 thereby losing contact with the wing (in particular the inner side of the wing.

Figure 10:
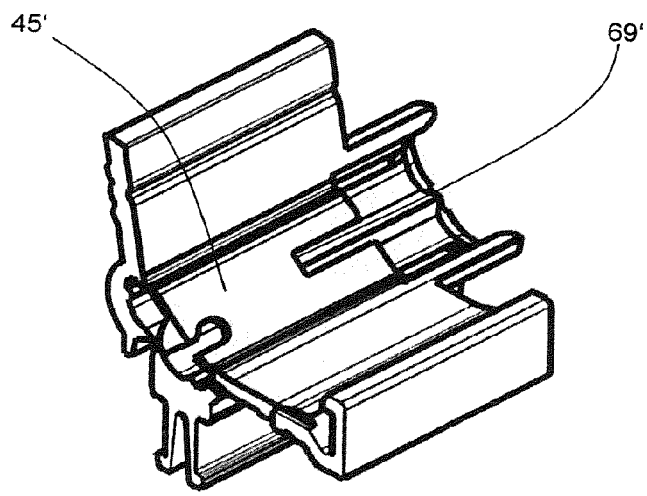
FIG. 10: shows a device according to the invention with an alternative covering element design in an open position: (a) shows a view obliquely from the front, (b) shows a view obliquely from behind.
Figure 10:
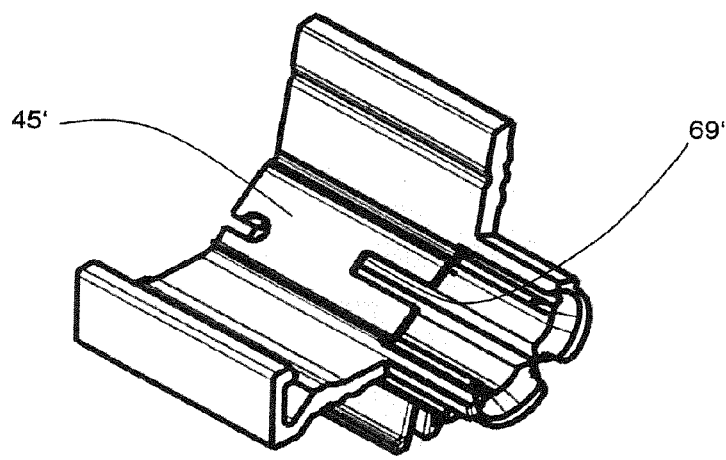

In an alternative embodiment (FIG. 10), the covering element 45', which can be shortened as shown at the rear part of the cartridge in the longitudinal direction with respect to the half-shells 13, 15, has at the rear center a slot or a slot-like recess. In this recess, a plunger of an injector can be pushed up to the stop and thus up to an inserted lens, if necessary the lens body, without necessitating the lifting or otherwise displacing of the covering element. The recess is functionally advantageously approximately 1 to 3 mm, or 1.5 to 2.5 mm wide.

In the closed position of the cartridge 3 (FIG. 3), the covering element 45 lies substantially outside the enclosed chamber 39 formed by the chamber 46, and may be between the wings 25, 27. A closure 73, in particular a snap closure, is formed on the wings 25, 27.

A plug device 75 is formed on the half-shell 15. This plug device 75 is used for insertion into an opening of an injector housing 1. Spring hooks 77, 77' with barbs serve, for example, as blocking agents. Thereby is created after insertion of the cartridge 3 into the injector housing 1 a fixed connection between these two parts.

Figure 6:
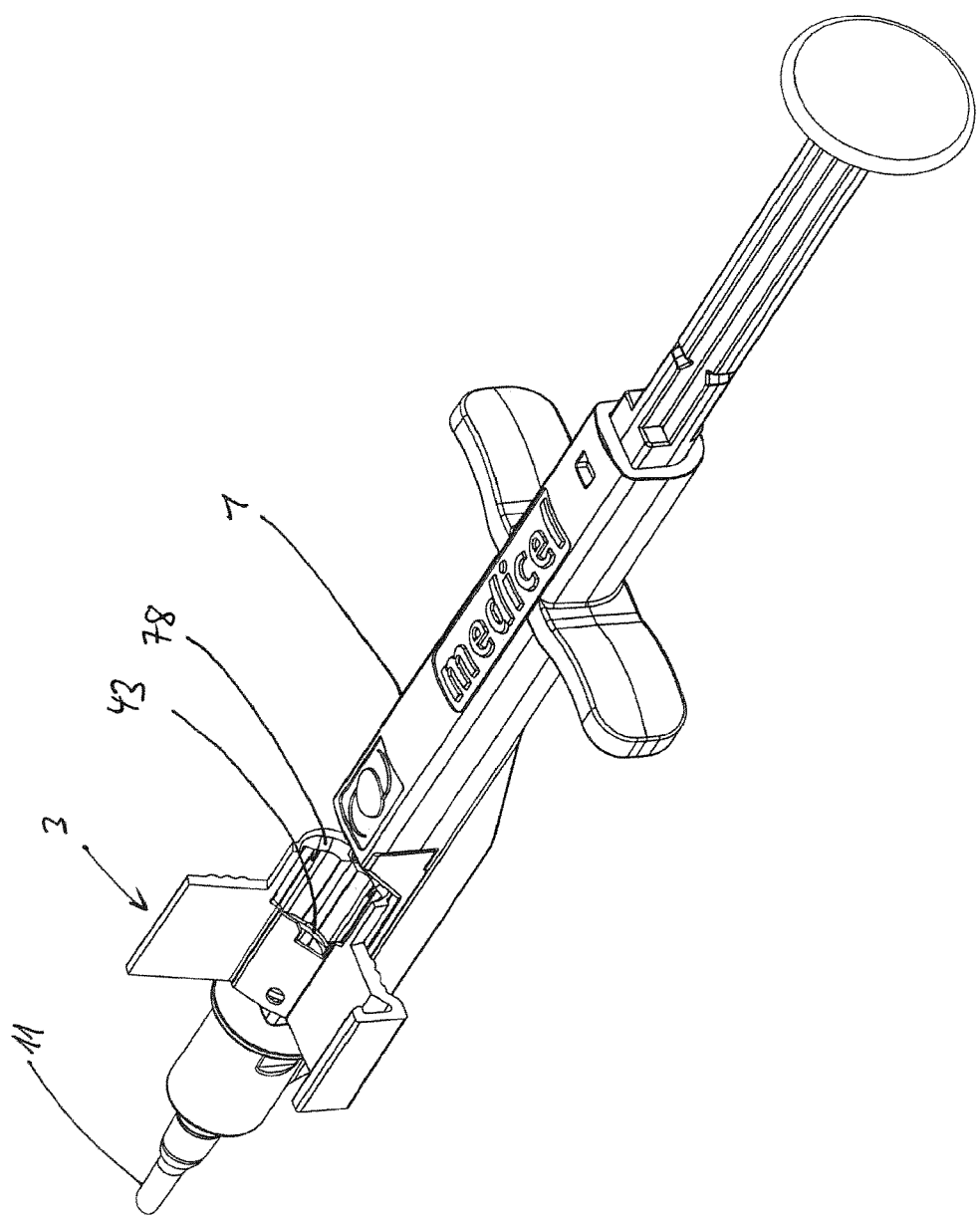
FIG. 6: shows an oblique view of an injector with inserted inventive device in the open position.
Figure 7:
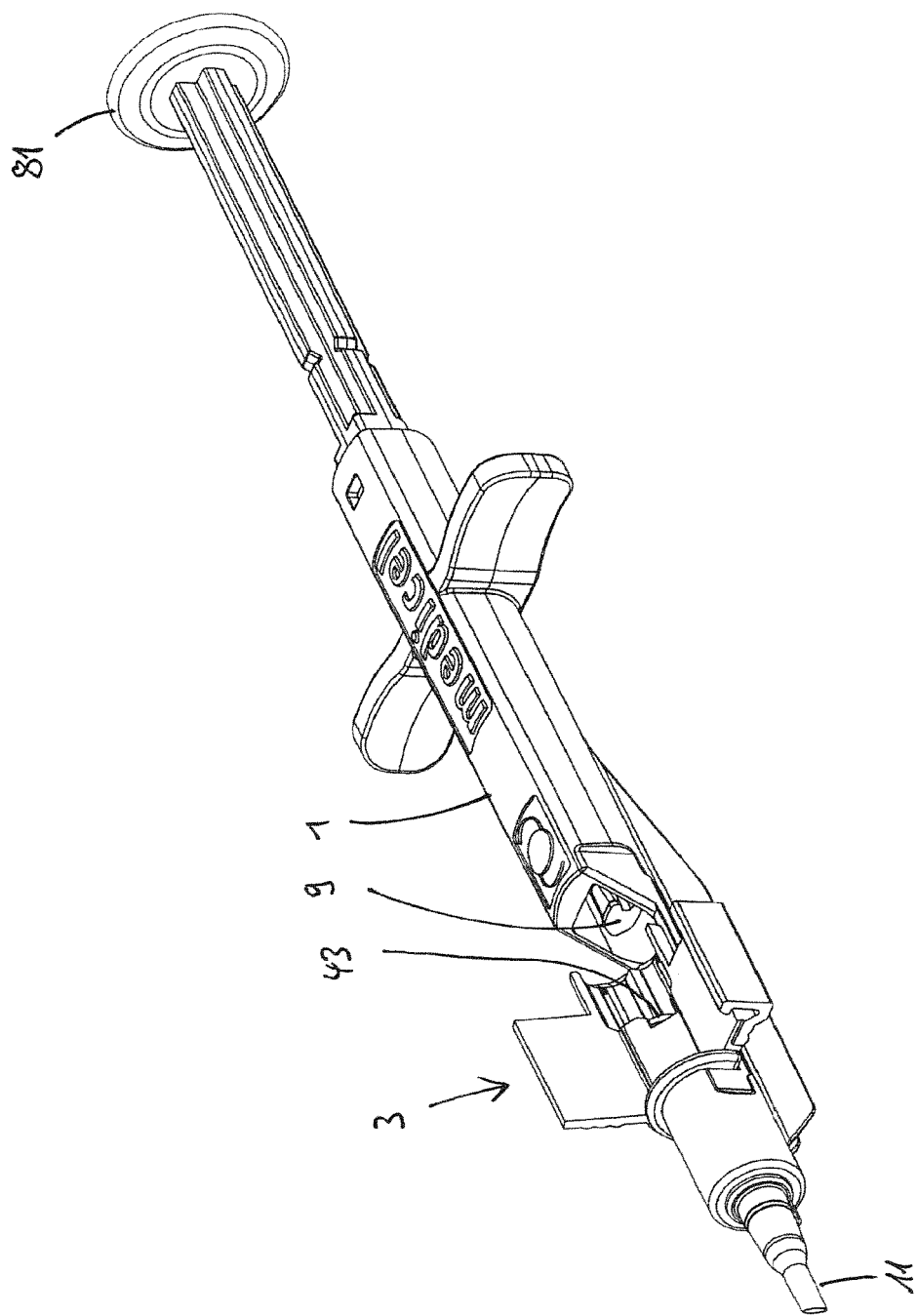
FIG. 7: shows a further oblique view of an injector with inserted inventive device in the open position.
Figure 8:
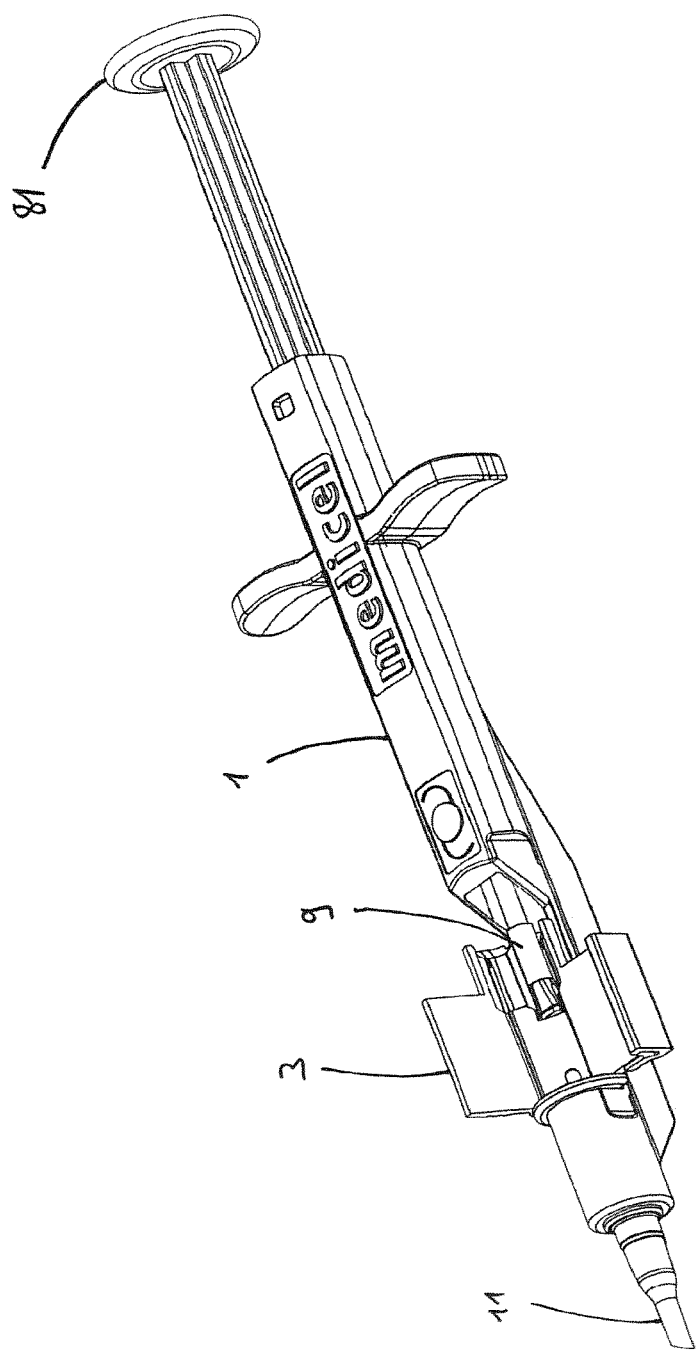
FIG. 8: shows a further oblique view of an injector with inserted inventive device in the open position.

The injector shown in FIGS. 6 to 9 substantially comprises an injector housing 1 and the plunger 9 displaceable therein for transporting and ejecting of the lens 33. In the illustrated embodiment, the cartridge 3 and optionally the injector nozzle 11 are represented as separately usable parts in the injector housing 1, however they may also be formed as one part. FIG. 6 and FIG. 7 show an injector with a cartridge 3 in the injector housing 1, said cartridge being occupied by a lens 33 (only the rear haptic 43 of the lens 33 can be seen). The plunger 9 is mounted in a starting position in the injector housing (not visible in FIG. 6), and may be locked, such that it does not interfere with insertion of the cartridge 3. At the rear end 7 (proximal) of the cartridge 3, i.e. the half-shells 13, 15, a bevel 78, 78' may be optionally formed peripherally to the inner surfaces 17, 19, said bevel serving for the introduction of the plunger 9. In FIG. 8, the plunger 9 can be seen in a position pushed partly into the injector. In this partially pushed-in position, the plunger 9 extends to the rear edge or stop 69 of the covering element 45. In this position of the plunger 9, the lens 33 is optionally pressed together with the front and rear haptics 43', 43. The lens 33 and haptics 43, 43' are thereby positioned under the covering element 45 in the chamber 46; i.e. the haptics are not protruding in any direction. An axial displacement of the lens 33 is prevented on the one hand by the stopper 59 and on the other hand by the plunger 9. The plunger 9 may optionally be locked in the injector housing 1. It is thus possible that the injector may already be provided at the factory with the lens 33 to be used. This may be an option, for example, for dry-stored lenses. Before the operation, therefore, the cartridge need only be closed by the surgeon or the assistant thereof, in that the first wing 25 is moved against the second wing 27, in order to thereby fold the lens 33 and push the covering element 45 out of the channel 46 (or out of the forming channel 39).

In a further embodiment (not shown in the figures), the carriage has a stopper on two sides of the covering element 45 (in particular on or near the front end face and on or near the rear end face of the cartridge). The stopper is thereby located on the covering element itself, wherein with respect to the orientation of the cartridge, one stopper is functionally advantageously arranged on the front edge, and one stopper on the rear edge of the covering element. This allows, for example, the storing of the lens in the cartridge (i.e. preloaded lens). Such a preloaded lens can optionally be stored in a container filled with sterile liquid such that the lens cannot thereby fall out of the cartridge. After opening of the container, the cartridge is removed from this container and inserted into the injector housing 1. Here, too, the cartridge can now be closed (as is described above), wherein the covering element 45 is pushed laterally with the stopper out of the channel 46 (or out of the forming channel 39).

If, in the case of the partially pushed-in plunger 9, the lens 33 with the lens body 41 and haptics 43, 43' is positioned under the covering element 45, the cartridge 3 may advantageously be closed, without pinching the lens body 41 or the haptics 43, 43' between the edges 21 and 23 or between the wings 25 and 27 of the cartridge during the closing process. The closing process of the cartridge takes place in particular as follows: The wings 25, 27 of the cartridge 3 are brought together, such as by hand. The covering element 45 thereby slides from its locked position at the edge 23, in particular out of the groove 56, onto the inside wing surface 28 of the second wing 27 and along this wing surface 28 out of the closing cavity 46 and out of the forming cavity 39.

Figure 9:
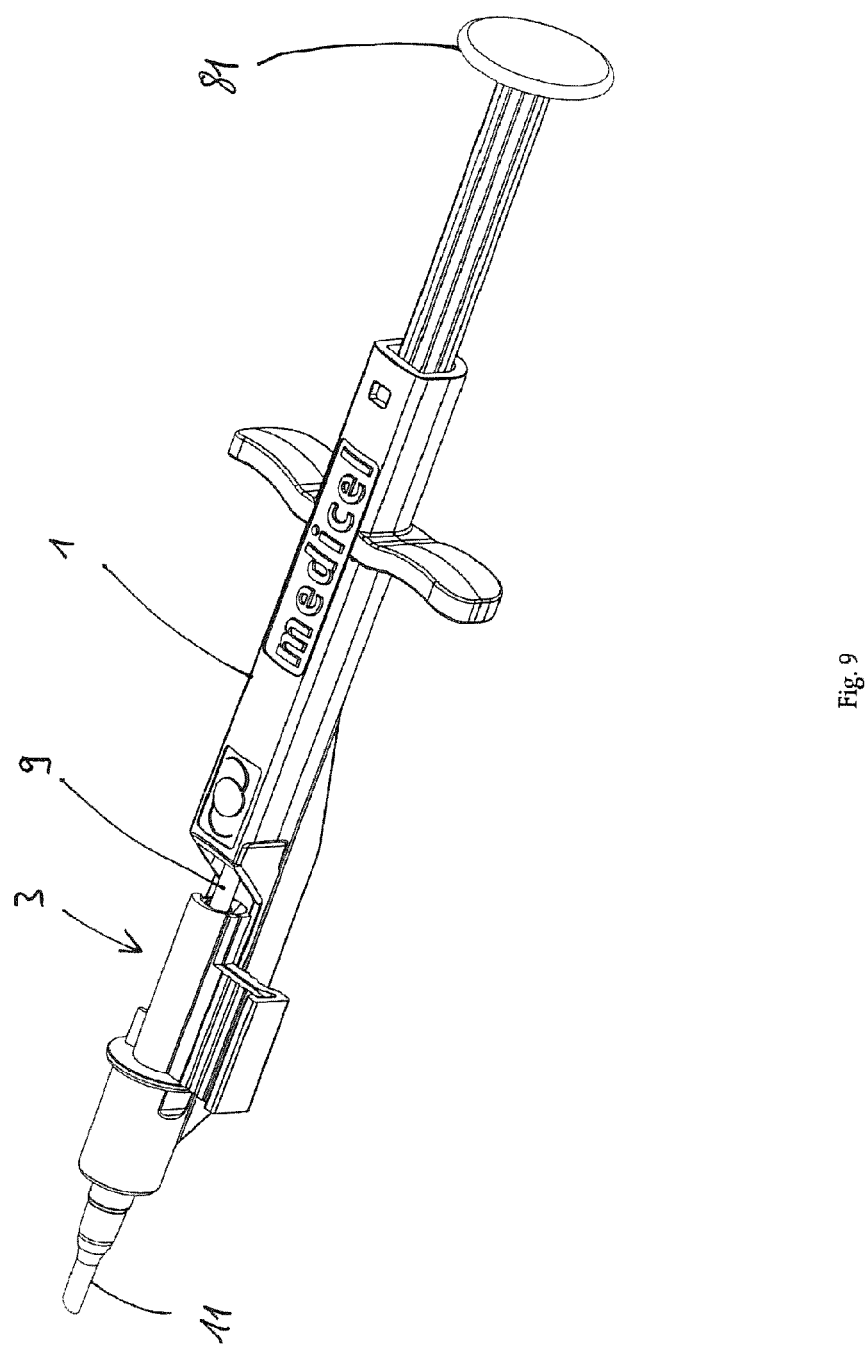
FIG. 9: shows an oblique view of an injector with inserted inventive device in the closed position.

In FIG. 9 can be seen the injector with closed cartridge 3 and partially pushed-in plunger 9. As the plunger 9 is only partially pushed into the cartridge 3, it can be seen there that the plunger end 81 (with respect to FIG. 8) protrudes with an unchanged length from the injector housing 1. In this position, the lens 33 is ready for injection. Through the pushing forward of the plunger 9, the lens 33 is pushed out through the cannula (injector nozzle) 11, in order to thereby be injected, for example, into an eye.

Figure 2A:
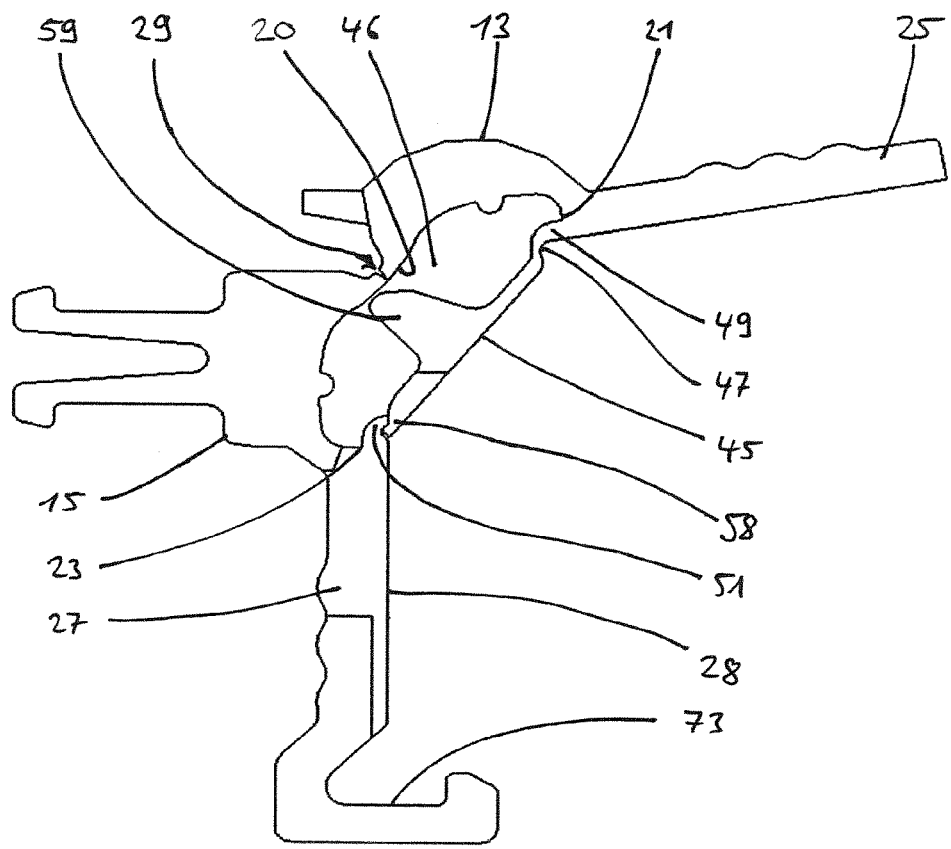
FIG. 2a: shows a front view of the device according to the invention in the open position.
Figure 2B:
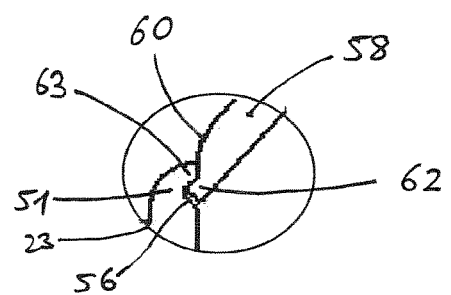
FIG. 2b: shows a section of FIG. 2a of the supporting connection between the free end of the covering element and the edge of a second half-shell.

In a further embodiment (not shown in the figures), the plate-shaped covering element 45 is replaced by at least one arm, in particular through one arm or two arms, wherein in the open position of the cartridge 3, the arm or each of the arms spans the loading surface 20 from the longitudinal edge 21 of the first half-shell 13 to the longitudinal edge 23 of the second half-shell 15. Stoppers, which are formed on the arm or each of the arms, serve (as is described above with reference to the covering element 45) to secure the position of the lens 33, in particular also the haptics thereof. The arm or arms are in particular designed such that the stopper or stoppers 59 are arranged as described above and shown in the figures. In particular, the stopper is may be formed as a protuberance of the arm, which protrudes from the arm on the inside of the half-shells (i.e. pointing to the side of the inner surfaces 17, 19 of the half-shells 13, 15 and thus to the inner surfaces 17, 19 of the half-shells 13, 15) when the cartridge is open (in particular when the free end of the arm lies on the second edge 23 or on the second strip 51). FIG. 2a and FIG. 2b show in particular a front view of the device according to the invention, wherein this front view equally represents a device with a holding element 45 formed as a plate-shaped covering element or formed as an arm. In each case it is functionally advantageous that the stopper 59 escapes from and glides out of the forming ejection passage (as well as the extension thereof) during the transition to the closed position of the chambers 13 and 15. In the example shown in FIG. 2a, the stopper escapes in particular due to its terminal position in the cartridge, which enables the stopper to move during the transition to the closed position of the chambers 13 and 15 along the front end face of the second longitudinal edge 23 and the wing 27 of the second half-shell 15 into the recess 61. Functionally advantageously, the end face of the second longitudinal edge 23 and the wing 27 of the second half-shell 15 are set back, the result of which is the frontal recess 61. In a non-terminal cartridge position of the stopper, a recess could be formed as a track in the edge 23 and wing 27 in the orthogonal direction relative to the axis of rotation of the first and second joints 29 and 47.

The covering element, in particular the arm or the plate-shaped covering element 45, may be generally designated as a holding element for the stopper.

In summary, the following can be stated:

A device for folding an intraocular lens 33 comprises two half-shells 13, 15 connected by a hinge 29, where the half-shells can be moved relative to one another and closed against one another, for example by means of wings 25, 27 formed on the half-shells, in order to fold an inserted intraocular lens 33 and simultaneously hold said lens ready for injection in a loading carrier channel which is formed by the closing of the half-shells 13, 15. Furthermore, the device for folding may comprise a holding element (in particular designed as an arm (not explicitly shown in the figures) or a covering element 45), which in an open position of the half-shells 13, 15 forms a bridge over the inner surfaces 17, 19 of the half-shells 13 and 15 from a first longitudinal edge 21 on the first half-shell 13 to a second longitudinal edge 23 on the second half-shell 15. Pinching of the lens 33, in particular of the lens body 41 or the haptics 43, 43' may thereby be prevented, in that the holding element (in particular when it is designed as a covering element 45) lies over the lens before and during folding, secures the lens on the half-shells and thereby prevents the lens (in particular during folding, i.e. during closing of the two half-shells) from penetrating into the intermediate space between the edges 21 and 23 and/or between the wings 25 and 27. This is supported here by the indentation-like configuration (indentation 53, 55) of the half-shells 13, 15 at the two longitudinal edges 21, 23, which partially frame the lens.

During closing of the two half-shells 13, 15, the holding element (in particular the covering element 45 or the arm) and optionally the stopper or stoppers 59 slide out of the forming loading channel (i.e. cavity 36) or away from the forming loading channel, in order not to interfere with the subsequent ejection of the lens or the injection thereof into an eye.

The invention will be explained hereinafter with reference to examples.

Example of Use 1

Case of Application and Problem:

Due to the simple, rarely erroneous loading of a lens from the rear into a self-contained injection cartridge, this type of loading the injection cartridge from the rear is preferred by many users. In known injection cartridges which are loaded from the rear, however, rigid piston ends must be used in order to inject the lens into the eye. The problem of rigid piston ends is that they can damage the lens, in particular if the lens is to be transplanted into the eye on which is to be operated by the smallest possible incision, since the thinner the piston end, the greater the risk that the piston end possibly erroneously penetrates the lens or at least bends or scratches it.

In the use of an injection cartridge which is fitted from behind, the intraocular lens cannot be prefolded, for which reason the lens must be folded during pushing forward by the pusher by means of the inner geometry of the injection nozzle. Due to the tapered geometry from the cross section of the lens up to the incision diameter, a piston (herein also called a plunger) with a flexible and form-fitted end (pusher) cannot be used. A flexible pusher specifically must form a positive engagement with the cartridge, otherwise there exists a very high risk that during pushing forward of the pusher, the rear lens haptic is pinched between the pusher and the wall of the cartridge. The volume of such a flexible pusher would be so large, however, that this would need to strongly compress during pushing forward of the piston and as a result thereof can lead to a penetration of the pusher by the tip of the piston as well as to deformation and a shearing off of the pusher. The necessary forces for the compression of the pusher would additionally cause the force of injection for the user to rise to an unacceptable level.

Inventive Solution to the Problem:

According to the invention, a loading chamber with an integrated lens holder with a lens cover (covering element) is used as part of an injection system.

In the described case of application, a system which is loaded from the rear, the loading chamber is open to the rear and allows the user to fit the loading chamber with the intraocular lens from the rear. The lens cover thereby acts as an insertion aid for the lens. After inserting of the lens and the use of a viscoelastic as a sliding aid, the loading chamber is closed, the lens is thereby prefolded and the lens cover is automatically folded by means of a hinge mechanism between the two wings of the loading chamber. Through this prefolding, the cross section is significantly reduced with respect to injection cartridges corresponding to the current state of the art, and a flexible pusher which is form-fitting and which does not damage the lens can thus be used. This flexible pusher is pushed forward subsequent to the folding process, whereby the lens can thus be injected into the eye.

Example of Use 2

Case of Application and Problem:

In a preloaded system, the intraocular lens must be protected during transport and storage against slipping or sliding out of the injector cartridge or the loading chamber. This is realized by a lens holder. However, a commercially available lens holder has the disadvantage that the user must remove this himself. An uncareful removal may lead to dislocation of the lens. Since in a preloaded system the user cannot make or should not make manipulations to the lens, this may lead thereafter to a pinching of the lens or the haptics thereof in the closing process of the loading chamber or during the subsequent pushing forward of the pusher. In addition, the removal of the lens holder represents an additional step for the user. In order to make the system as easy and comfortable for the user as possible, this additional step of removal of the lens holder should be omitted wherever possible.

Inventive Solution to the Problem:

According to the invention, a loading chamber with an integrated lens holder with a lens cover (covering element) is used as part of an injection system.

In the described case of application, a preloaded system, the loading chamber is completely or at least partially closed to the rear, above, and also to the front for storage and transport. In the case of dry-stored lenses, the loading chamber according to the invention is already inserted into the injector. In the case of liquid-stored lenses, the loading chamber according to the invention is stored in a liquid-filled container. It is removed therefrom by the user and inserted into the injector. In both lens types, the loading chamber is closed after injection of a viscoelastic, the lens is thereby prefolded and the lens cover is folded by means of a hinge mechanism between the two wings of the loading chamber. Subsequently, the flexible pusher can be pushed forward and the lens can be injected into the eye. The integration of the lens holder and the automatic folding thereof is accompanied by the advantage that the user saves an operational step and thus time, thereby also excluding potential error through the previously necessary removal of the lens holder and additionally eliminating the risk during folding of a haptic slipping out and being pinched between the two wings.

While specific embodiments have been described above, it is apparent that different combinations of the identified possible embodiments may be used, insofar as these possible embodiments are not mutually exclusive.

While the invention has been described with reference to specific embodiments, it is apparent that changes, modifications, variations and combinations can be made without deviating from the inventive concept.

The invention claimed is:

1. A device for receiving an intraocular lens, comprising: a first half-shell and a second half-shell connected to each other in an articulating manner by a first joint, the first and second half-shells movable relative to each other from an open position to a closed position, the first and second half-shells forming an open chamber in the open position, to allow for insertion of a lens into the open chamber and forming an enclosed chamber in the closed position, the enclosed chamber defining an ejection passage for ejecting the lens from the enclosed chamber;
a holding element coupled to the first half-shell, the holding element spanning at least a portion of the open chamber in the open position and displaceable by the first half-shell to a position away from the enclosed chamber in the closed position; and
at least one stopper attached to the holding element, the at least one stopper displaceable by the holding element outside the enclosed chamber in the closed position.

2. The device of claim 1, wherein the at least one stopper is attached to the holding element so that when the holding element is displaced, the at least one stopper moves along an edge of the second half-shell.

3. The device of claim 1, wherein the holding element is connected to the first half-shell via a second joint, which forms a hinge.

4. The device of claim 1, further comprising a bending groove formed on a side of the holding element that bends away from an inner surface of the first half-shell when the first and second half-shells are moved from an open position to a closed position.

5. The device of claim 1, further comprising a holding element support on a second longitudinal edge of the second half-shell.

6. The device of claim 1, wherein upon closing of the first and second half-shells, the holding element slides over a second longitudinal edge of the second half-shell and out of the closing chamber.

7. The device of claim 6, wherein in the closed position, the holding element is located substantially outside the enclosed chamber.

8. The device of claim 7, wherein in the closed position, the holding element is located between first and second wings.

9. The device of claim 1, further comprising at least one additional holding element, wherein the at least one additional holding elements supports at least one additional stopper.

10. The device of claim 1, wherein the at least one stopper comprises a first stopper for a front haptic of the lens and a second stopper for a rear haptic of the lens.

11. The device of claim 1, wherein the holding element is integrally formed with the first and second half shells.

12. The device of claim 1, wherein the first and second half-shells each include a support.

13. The device of claim 12, wherein the support forms a side rail.

14. The device of claim 1, wherein the enclosed chamber in the closed position of the first and second half-shells forms a loading channel.

15. The device of claim 1, further comprising first and second wings arranged respectively on longitudinal edges of the first and second half shells.

16. The device of claim 15, further comprising a closure formed on each of the first and second wings.

17. The device of claim 1, further comprising a plug device formed on one of the first and second half-shells for inserting into a receiving opening of an injector housing.

18. The device of claim 1, wherein the device forms a cartridge configured for insertion into an injector.

19. The device of claim 1, wherein the device comprises a cartridge configured for use with an injector housing and a plunger, the plunger being displaceable in a longitudinal direction in the injector housing.

20. The device of claim 1, wherein in the closed position of the first and second half-shells, the holding element is clamped between edges of the first and second half shells.

* * * * *